United States Patent
Crost et al.

(10) Patent No.: US 7,056,458 B2
(45) Date of Patent: Jun. 6, 2006

(54) NON-THROMBOGENIC SEMIPERMEABLE MEMBRANE AND METHOD FOR MAKING SAME

(75) Inventors: Thierry Crost, St. Maurice de Gourdans (FR); Jean-Louis Renaux, Caluire (FR); Michel Thomas, Sérezin du Rhône (FR)

(73) Assignee: Hospal Industrie, Meyzieu Cedex (FR)

(*) Notice: Subject to any disclaimer, the term of this patent is extended or adjusted under 35 U.S.C. 154(b) by 419 days.

(21) Appl. No.: 09/937,558

(22) PCT Filed: Jan. 26, 2001

(86) PCT No.: PCT/FR01/00248

§ 371 (c)(1),
(2), (4) Date: Jan. 3, 2002

(87) PCT Pub. No.: WO01/54802

PCT Pub. Date: Aug. 2, 2001

(65) Prior Publication Data

US 2003/0021826 A1    Jan. 30, 2003

(30) Foreign Application Priority Data

Jan. 27, 2000    (FR) .................................. 00 01065

(51) Int. Cl.
*B05D 5/00* (2006.01)
*B01D 63/02* (2006.01)
*B01D 71/42* (2006.01)

(52) U.S. Cl. ..................... 264/48; 264/49; 210/500.24; 210/500.27; 210/500.43; 210/650; 210/500.23; 210/490; 427/245; 427/246

(58) Field of Classification Search ................ 210/483, 210/488, 489, 490, 500.23, 500.24, 500.27, 210/500.43, 650; 264/48, 49; 427/245, 427/246

See application file for complete search history.

(56) References Cited

U.S. PATENT DOCUMENTS 4,749,619 A * 6/1988 Angleraud .................. 428/398

(Continued)

FOREIGN PATENT DOCUMENTS

DE    42 40 681 A1    6/1994

(Continued)

OTHER PUBLICATIONS

T. Masai et al., "Experimental Evaluation of Terumo[R] Heparin-Coated System For Heparinless ECMO Using a Very Low Blood Flow Model", Osaka University, Thermo Corp., Japan, 1 page, (1994), ASA10.

(Continued)

*Primary Examiner*—John Kim
*Assistant Examiner*—Krishnan S. Menon
(74) *Attorney, Agent, or Firm*—Finnegan, Henderson, Farabow, Garrett & Dunner, L.L.P.

(57) ABSTRACT

The invention concerns a non-thrombogenic semipermeable membrane comprising a support semipermeable membrane and an anticoagulant suitable for treating blood and plasma by extracorporeal circulation. The invention is characterized in that: the support membrane is made essentially of a polyacrylinitrile, bearing anionic groups or groups capable of being anionic; the surface of the support semipermeable membrane designed to be in contact with blood or plasma is coated successively with a cationic polymer and an anticoagulant. The invention also concern an exchanger for treating blood or plasma by extracorporeal circulation comprising two sections separated by a non-thrombogenic semipermeable, membrane and a method for making the exchanger.

5 Claims, 4 Drawing Sheets

U.S. PATENT DOCUMENTS

| | | | | |
|---|---|---|---|---|
| 4,800,016 | A | | 1/1989 | Yang .......................... 210/206 |
| 5,015,226 | A | | 5/1991 | Polaschegg ..................... 604/4 |
| 5,421,815 | A | | 6/1995 | Noguchi et al. ................ 604/4 |
| 5,455,040 | A | | 10/1995 | Marchant |
| 5,632,897 | A | | 5/1997 | Mathieu ...................... 210/645 |
| 5,637,081 | A | | 6/1997 | Noguchi et al. ................ 604/4 |
| 5,672,638 | A | | 9/1997 | Verhoeven et al. ......... 523/112 |
| 5,679,659 | A | | 10/1997 | Verhoeven et al. ............ 514/56 |
| 5,709,993 | A | | 1/1998 | Buturovic-Ponikvar ........ 435/2 |
| 5,718,726 | A | | 2/1998 | Amon et al. .................... 623/2 |
| 5,820,917 | A | | 10/1998 | Tuch .......................... 427/2.1 |
| 5,840,190 | A | * | 11/1998 | Scholander et al. ... 210/500.24 |
| 5,885,609 | A | | 3/1999 | Amiji ......................... 424/425 |
| 6,010,475 | A | * | 1/2000 | Thomas et al. ............ 604/6.09 |
| 6,177,013 | B1 | * | 1/2001 | Thomas et al. ............. 210/650 |

FOREIGN PATENT DOCUMENTS

| | | |
|---|---|---|
| DE | 42 40 681 C2 | 6/1994 |
| EP | 0 282 091 A2 | 9/1988 |
| EP | 0 769 503 A2 | 4/1997 |
| EP | 0 878 491 A2 | 11/1998 |
| EP | 0 925 826 A1 | 6/1999 |
| WO | WO 93/05825 | 4/1993 |
| WO | WO 96/35954 | 11/1996 |
| WO | WO98/08552 | 3/1998 |
| WO | WO98/10805 | 3/1998 |
| WO | WO98/10806 | 3/1998 |
| WO | WO98/46288 | 10/1998 |
| WO | WO98/53829 | 12/1998 |

OTHER PUBLICATIONS

R.J. Caruana et al., "Anticoagulation", Handbook of Dialysis, 2$^{nd}$ Edi., pp. 121-136 and 160-163.

J. Vienken et al., "Interactions of Heparin With Positively-Charged Membranes Allow Heparin-Free Dialysis", Asaio, 12 pages, (1994).

K. Eya et al., "Total Heart-Lung Replacement With an Artificial Heart-Lung System", ASAIO, 1 page, 1994.

K. AL-Lamee et al., "New Methods For Surface Modification and Covalent Attachment of Heparin", Medical Device Technology, pp. 24-27, (1998).

A. Usui, et al., "Heparin Coating Extends the Durability of Oxygenators Used for Cardiopulmonary Support", Artificial Organs, pp. 840-844, (1999).

R.H. Barth, et al., "Heparin-Free Hemodialysis With a Polyacrylonitrile Membrane", Trans Am Soc Artif. Intern Organs, pp. 597-600, (1989).

H.W.M. Ten Hoopen et al., "Sterilization of Heparinized Cuprophan Hemodialysis Membranes", Journal of Materials Science: Materials in Medicine, vol. 7, pp. 699-704, (1996).

G. Remuzzi, M.D., "AN69 Membrane For Hemodialysis: Long Term Effects on the Uremic Hemostatic Abnormalities", 1$^{st}$ American AN69 Membrane Scientific Exchange, pp. 83-89, (1982).

S.K. Mujais et al., "Heparin Free Hemodialysis Using Heparin Coated Hemophan", ASAIO Journal, vol. 42, pp. M538-M541, (1996).

O. Larm, et al., "A New Non-Thrombogenic Surface Prepared by Selective Covalent Binding of Heparin VIA a Modified Reducing Terminal Residue", Biomat., Med. Dev., Art. Org., vol. 11 (2&3), pp. 161-173 (1983).

C. Charbonnel et al., "A Dialyse Sans Héparine", Session Nationale, pp. 10-11, (1994).

Dr. Ph. Morinière, Anticoagulation des Circulations Extra-Corporelles Pour Épuration Extra-Rénale, Rappels sur l'hémostase et ses tests, pp. 1-39, (1998).

G. Soula, "Le Collagène Modifié Empêche L'Adhésion des Tissus", Industries et Techniques, No. 804, pp. 66-68, (1999).

J. Pélissié, "Héparinisation de Surface", RMB, vol. 16, pp. 290-291, (1994).

Baxter, "The Considered Approach to Haemofiltration," A brochure from Baxter (6 pages).

Baxter, "New Frontiers in Biocompatibility", Baxter Healthcare Corporation, (7 pages) (1996).

W. L. J. Hinrichs, et al. "*In Vitro* Evaluation of Heparinized Cuprophan Hemodialysis Membranes," Journal of Biomedical Materials Research, vol. 35, pp. 443-450 (1997).

B. Urlesberger et al., Activation of the Clotting System: Heparin-Coated Versus Non Coated Systems For Extracorporeal Circulation, The International Journal of Artificial Organs, vol. 20, No. 12, pp. 708-712 (1997).

C. Ronco, et al., "Alternative Treatment Strategies for Acute Renal Failure: Continuous Arteriovenous Hemofiltration With AN69S Membrane: Procedures and Experience," Kidney International, vol. 33, Suppl. 24, pp. S-150-S-153 (1988).

A. K. Cheung, et al., "Modulation of Complement Activation on Hemodialysis Membranes by Immobilized Heparin," Journal of the American Society of Nephrology, vol. 2, No. 8, pp. 1328-1337 (1992).

M. Erdtmann, et al., "Photochemical Immobilization of Heparin, Dermatan Sulphate, Dextran Sulphate and Endothelial Cell Surface Heparan Sulphate onto Cellulose Membranes for the Preparation of Athrombogenic and Antithrombogenic Polymers," Biomaterials, vol. 15, No. 13, pp. 1043-1048 (1994).

C. J. Shanley, et al., "Prolonged Extracorporeal Circulation Without Heparin: Evaluation of the Medtronic Minimax Oxygenator," ASAIO Journal, 38, pp. M311-M316 (1992).

K. Mottaghy, et al., "Heparin-Coated Versus Non-Coated Surfaces for Extracorporeal Circulation," The International Journal of Artificial Organs, vol. 14, No. 11, pp. 721-728 (1991).

A. Piao, et al., "Heparin Immobilization by Surface Amplification," ASAIO Journal, pp. M638-M643 (1992).

F. Keller, et al., "Risk Factors of System Clotting in Heparin-Free Haemodialysis," Nephrol Dial Transplant, vol. 5, pp. 802-807 (1990).

H. Sperschneider, et al., "Impact of Membrane Choice and Blood Flow Pattern on Coagulation and Heparin Requirement—Potential Consequences on Lipid Concentrations," Nephrol Dial Transplant, vol. 12, pp. 2638-2646 (1997).

J. C. Bos, et al., "Low Polymorphonuclear Cell Degranulation During Citrate Anticoagulation: A Comparison Between Citrate and Heparin Dialysis," Nephrol Dial Transplant, vol. 2, pp. 1387-1393 (1997).

J. E. Romão Jr., et al. "Haemodialysis Without Anticoagulant: Haemostasis Parameters, Fibrinogen Kinetic, and Dialysis Efficiency," Nephrol Dial Transplant, vol. 12, pp. 106-110 (1997).

F. Keller, et al., "Thromboxane B$_2$ Blood Levels and Incipient System Clotting in Heparin Free Hemodialysis," ASAIO Journal, vol. 41, pp. 173-177 (1995).

P. M. Ambühl, et al., "Plasma Hypercoagulability in Haemodialysis Patients: Impact of Dialysis and Anticoagulation," Nephrol Dial Transplant, vol. 12, pp. 2355-2364 (1997).

K. E. Otte, et al., "Does the Method of Heparinisation Influence the Biocompatibility of Dialysis Membranes?" Nephrol Dial Transplant, vol. 6, pp. 62-65 (1991).

R. Blezer, et al., "Activation of Blood Coagulation at Heparin-Coated Surfaces," Journal of Biomedical Materials Research, vol. 37, pp. 108-113 (1997).

H. Miyama, et al., "Antithrombogenic Heparinized Polyacrylonitrile Copolymer ," Journal of Biomedical Materials Research, vol. 20, pp. 895-901 (1986).

J. A. Summerton, et al., "*In Vitro* Clotting Technique for Hemodialysis Circuits," ASAIO Journal, p. 109 (1999).

N. Gretz, et al. "Heparin Binding by Hemophan Membranes," Dialysis Clinic, p. 128 (date unknown).

L. M. Robertson, et al., "Modification of the Blood Compatibility of Hemodialysis Membranes," Artificial Organs, vol. 14, Suppl. 2, p. 41 (1990).

S. Bowry, et al., "Heparin-Free Dialysis Following Pre-Rinsing of Hemophan With High Doses of Heparin," 31st EDTA, Vienna, p. 167, (Jul. 3-6, 1994).

L. Hsu, Ph.D., "Non-Thrombogenic Surfaces in Extracorporeal Devices," Abstracts of the IXth World Congress of ISAO/XXth Congress of ESAO, Amsterdam, p. 371 (Jul. 4-8, 1993).

C. Charbonnel, et al., "Dialysis Without Heparin," AFIDTN, vol. 34, Lyons, National Session, pp. 10-11, (1994) with Translation pp. 1-5.

Dr. Ph. Morinière, "Anticoagulatioin of Extracorporeal Circulations for Dialysis," pp. 1-52 (1997/1998) with Translation pp. 1-53.

"Modified Collagen Prevents Tissue Adhesion," Industries et Techniques, No. 804, pp. 66 (May 1999) with Translation p. 1.

J. Pélissié, "Surface Heparinisation," RBM, vol. 16(7), pp. 290-291 (1994) with Translation pp. 1-5.

S. Bowry, et al., "Heparin-Free Dialysis Following Pre-rinsing of Hemophan with High Doses of Heparin," 31st Edta, Vienna, Jul. 3-6, 1994, p. 167.

N. Gretz, et al., "Heparin Binding by Hemophan Membranes," *Dialysis Clinic*, p. 128.

Li-Chien Hsu, et al., "Non-Thrombogenic Surfaces in Extracoporeal Devices," *The International Journal of Artificial Organs*, vol. 16, No. 6, 1993, p. 371.

L. M. Robertson, et al., "Modification of the Blood Compatibility of Hemodialysis Membranes," *Artificial Organs* (Vol. 14, Suppl. 2), ISAO Press 1990, pp. 41-43.

J. A. Summerton, et al., "In Vitro Clotting Techniques for Hemodialysis Circuits," *ASAIO Journal* 1999, pp. 109-112.

David A. Lane, Ph.D. and Ulf Lindal, M.D., Ph.D., "Heparin Chemical and biological properties, clinical applications," *Surface Immobilized Heparin* 1999, p. 598.

* cited by examiner

NON-THROMBOGENIC SEMIPERMEABLE MEMBRANE AND METHOD FOR MAKING SAME

The present invention concerns the field of blood and plasma treatment by extracorporeal circulation, in particular by dialysis, haemofiltration and plasmapheresis. It relates to a composite semipermeable membrane comprising a semipermeable support membrane coated with an anticoagulant agent, which reduces the thrombogenic character of the support.

The present invention also relates to exchangers for treating blood or plasma by extracorporeal circulation, comprising this composite semipermeable membrane, as well as to methods for manufacturing these exchangers.

Throughout this text, the term "semipermeable membrane" is used to denote a flat semipermeable membrane or a bundle of semipermeable hollow fibres. Also, throughout this text, the term "exchanger" is used to denote an exchanger for treating blood or plasma by extracorporeal circulation, which generally comprises two compartments separated by a semipermeable membrane, each provided with two accesses, a first compartment being intended for the circulation of the patient's blood or plasma, and a second compartment being intended for the circulation of used liquid.

The treatment of a uraemic patient's blood or plasma requires the use of an extracorporeal blood circuit connected to an exchanger. The blood, in the extracorporeal circuit, is subjected to a major thrombotic risk which it is necessary to prevent by effective anticoagulation. This is why, even though the materials used for the manufacture of exchangers are selected to be as biocomoatible as possible so that, in particular, coagulation reactions do not take place or take place at a relatively benign levels, an anticoagulant agent, generally heparin (fractionated or non-fractionated) is customarily injected into the patient's blood.

The amount of heparin injected into the patient conventionally varies from 7500 to 11,000 international units (IU) per treatment session, or more in certain cases.

In common practice, the anticoagulation of blood rarely presents difficulties. In certain patients, however, heparin can cause undesirable secondary reactions, in particular haemorrhaging. Other side-effects reported in the literature are thrombocytopoenia (drop in the number of platelets) allergies, osteopoross (observed in the event of prolonged heparin adrinistration), increases in transaminases (hepatic enzymes) and hyperlipidaemia. Sensitivity to heparin is variable from one patient to another and as a function of time for a given patient.

For patients with a high risk of haemorrhaging, there is a method of extracorporeal blood treatment without an anticoagulant, which consists in preventing thrombosis of the blood in the extracorporeal circulation circuit and in the dialyser by frequently rinsing the circuit and the dialyser with physiological saline in order to flush therefrom the thrombi being formed. This method involves high blood circulation rates, which are not always tolerated by patients.

Furthermore, this treatment without an anticoagulant, which is technically difficult, requires specific training of the nursing staff, rigorous compliance with the operating protocol, strict monitoring of the dialysis in order to prevent incidents, and early detection of incidents so that they can be dealt with.

With a view to avoiding the injection of anticoagulant into the extracorporeal blood circuit, a great deal of research work has been undertaken in order to improve the haemocompatibility of semipermeable membranes by binding heparin to the surface of the membrane intended to be placed in contact with the blood, by means of ionic or covalent bonding (see J. Pelissié "Héparinisation de surface" [surface heparinization] in RMB (1994) 16, 7, 290–291).

The techniques described for the ionic binding of heparin aim to create quaternary amine groups on the surface of the semipermeable membrane to be treated. Heparin, which is negatively charged owing to its sulphate and carboxylic groups, can react with quaternary amine groups. However, rapid release of heparin due to the weakness of the intermolecular bonding has been observed, which presents the drawback of reducing the antithrombogenic character of the surfaces intended to be in contact with the blood and of promoting the appearance of undesirable side-effects due to freed heparin. In order to compensate for the continuous release of heparin, large amounts of this anticoagulant must be bound to the membrane, which makes it difficult to control the anticoagulation of the patient's blood and increases the cost.

The techniques described for covalent binding involve specific and complex chemical reactions allowing heparin to become attached to the surfaces of the materials intended to be placed in contact with the blood. These techniques, however, since they cause a substantial modification of the chemical nature of the materials, are not generally suitable for semipermeable membranes because they would risk provoking a significant reduction in the fundamental properties of these membranes, such as diffusive and convective transport capacities and the capacity for adsorbing undesirable substances. There is furthermore a risk of reducing the antithrombogenicity by inactivation of heparin.

The only exchanger marketed to date comprising a semipermeable membrane treated with an anticoagulant agent in order to reduce its thrombogenic character is the haemofilter with the brand name DURAFLO from the company BAXTER. This semipermeable membrane is based on polysulphone.

Certain semipermeable membranes consisting essentially of a copolymer of acrylonitrile and at least one anionic or anionizable monomer, which is o'efinically unsaturated, such as the copolymer manufactured by HOSPAL under the brand name AN69, are acknowledged to be much less thrombogenic than cellulosic membranes. The implementation of dialysis without heparin using these membranes requires, however, high blood circulation rates [at least 400 ml/min according to the article "Heparin-free hemodialysis with a polyacrylonitrile membrane", by Robert H. Barth et al., Vol. XXXV Trans Am Soc Artif Intern Organs (1989)], which is not always tolerated by all patients.

It is a first object of the present invention to reduce the thrombogenic character of semipermeable membranes consisting essentially of a copolymer of acrylonitrile and at least one anionic and anionizable monomer by binding an anticoagulant agent to these membranes, while keeping the other fundamental properties of these membranes at an acceptable level, that is to say their capacity for diffusive and convective transport (water permeability, selective permeability to molecules with a weight-average molecular weight less than that of albumin), their capacity for adsorbing undesirable substances and their mechanical properties.

It is a second object of the present invention to bind, stably, to the surface of semipermeable membranes consisting essentially of a copolymer of acrylonitrile and at least one anionic and anionizable monomer, an anticoagulant agent which can exert its anticoagulant activity without being eluted and released rapidly into the blood or plasma during the treatment by extracorporeal circulation.

It is a third object of the present invention to reduce the amount of anticoagulant agent injected into the patient during an extracorporeal blood treatment session carried out by means of an exchanger provided with a semipermeable membrane consisting essentially of a copolymer of acrylonitrile and at least one anionic and anionizable monomer, to which an anticoagulant agent is bound.

In order to achieve these objects, the present invention provides a composite semipermeable membrane comprising a semipermeable support membrane and an anticoagulant agent suitable for treating blood and plasma by extracorporeal circulation, characterized in that:

the semipermeable support membrane consists essentially of a polyacrylonitrile carrying anionic or anionizable groups;

the surface of the semipermeable support membrane intended to be placed in contact with the blood or plasma is coated successively:

with a cationic polymer carrying cationic groups which are capable of forming an ionic bond with the anionic or anionizable groups of the polyacrylonitrile, the cationic polymer comprising chains whose size is sufficient for them not to pass through the semipermeable support membrane; and with an anticoagulant agent carrying anionic groups which are capable of forming an ionic bond with the cationic groups of the said cationic polymer.

In certain cases, the present invention furthermore makes it possible to reduce the total amount of the bound or unbound anticoagulant agent needed for implementing an extracorporeal blood treatment session by means of an exchanger provided with a semipermeable membrane consisting essentially of a copolymer of acrylonitrile and at least one anionic and anionizable monomer, to which an anticoagulant agent is bound, and hence to reduce the cost of the treatment session and the undesirable side-effects of the anticoagulant agent.

According to the invention, the chains of the cationic polymer have a sufficiently large steric hindrance for them not to pass through the semipermeable support membrane, which makes it possible for these chains to become bound essentially to the surface of the membrane by ionic bonding. The amount of cationic polymer needed for treating the semipermeable support membrane is consequently moderate since a bulk treatment of the semipermeable support membrane with penetration of the cationic polymer into the pores is not required.

Preferably, the cationic polymer is prepared by ultrafiltration using a semipermeable membrane which is identical to the semipermeable support membrane or which has a cut-off threshold equal to or greater than that of the semipermeable support membrane, in order to exclude the cationic polymer chains capable of passing through the semipermeable support membrane.

The composite semipermeable membrane according to the invention has three major advantages:

firstly, the binding of the anticoagulant agent by ionic bonding takes place almost only at the surface of the semipermeable membrane. The bound anticoagulant agent, which is accessible to the coagulation proteins, can consequently exert an effective anticoagulant activity during a session of blood and plasma treatment by extracorporeal circulation;

secondly, the coagulation time (KCT, for activated cephalin time) of blood or plasma purified with the aid of the composite semipermeable membrane is fairly close, or equivalent, to that of normal blood or plasma not supplemented with an anticoagulant agent.

thirdly, the thrombogenic character of the composite semipermeable membrane is very greatly reduced when comparing it with that of the semipermeable support membrane which it contains.

According to one variant of the invention, the cationic polymer is a polyamine which is preferably hydrophilic and carries primary, secondly, tertiary or quaternary amine groups. The cationic polymer is preferably a polyethyleneimine (PEI). The amount of PEI deposited and bound can vary between approximately 1 mg and approximately 30 mg per $m^2$ of membrane (including the end points).

The anticoagulant agent suitable for the invention must not be toxic.

According to another variant of the invention, the anticoagulant agent carrying anionic groups belongs to the family of glycoaminoglycans having an anticoagulant activity. Preferably, this agent essentially consists of heparin (fractionated or non-fractionated). The amount of heparin deposited and bound can vary between approximately 200 IU and approximately 20,000 IU per $m^2$ of membrane (including the end points), preferably between approximately 500 IU and approximately 10,000 IU per $m^2$ of membrane (including the end points). The amount of heparin bound is selected according to the type of treatment for which the exchanger is intended:

intermittent treatment (session of from 3 to 6 hours) for patients suffering from chronic or acute renal insufficiency or continuous treatment (12 to 96 hours) for patients suffering from acute renal insufficiency;

treatment during which no anticoagulant agent is injected into the patient's vascular circuit.

The amount of heparin bound is less than the amount of heparin which is injected into the patient during a conventional treatment (which as of the order of from 7500 to 11,000 IU or more in the event that the membrane is rinsed with a heparin solution before the blood is circulated in the extracorporeal circuit).

The invention is suitable for the preparation of composite semipermeable membranes from a semipermeable support membrane consisting essentially of a polyacrylonitrile carrying anionic or anionizable groups which are selected from sulphonic, phosphonic, carboxylic, sulphuric, phosphoric groups and from the corresponding salified groups.

Preferably, the anionic or anionizable groups of the polyacrylonitrile are acid sulphonic groups or salified sulphonic groups.

Advantageously, the semipermeable support membrane consists essentially of a copolymer of acrylonitrile and sodium methallyl sulphonate, such as the copolymer with the brand name AN69 manufactured by HOSPAL, with which the best performance has been achieved.

The invention also relates to an exchanger for treating blood or plasma by extracorporeal circulation, comprising two compartments separated by a semipermeable membrane having a surface oriented towards a first compartment intended for the circulation of blood or plasma, characterized in that that the surface of the semipermeable membrane oriented towards the first compartment is coated successively with a cationic polymer and with an anionic anticoagulant agent.

The composite semipermeable membrane may be in the form of a flat membrane or a bundle of hollow fibres.

Preferably, the exchanger which comprises the composite semipermeable membrane according to the invention is sterilized and ready for use. It hence does not require any special handling by its user.

The present invention also relates to a method for reducing the thrombogenic character of an exchanger for treating blood or plasma by extracorporeal circulation, comprising two compartments separated by a semipermeable membrane having a surface oriented towards a first compartment intended for the circulation of blood or plasma, comprising the following successive stages:

(a) preparing a semipermeable membrane, In the form of a flat membrane or a bundle of hollow fibre, from a solution of polyacrylonitrile carrying anionic or anionizable groups;

(b) assembling the various components of the exchanger, in particular fitting the semipermeable membrane or a bundle of hollow fibres in a case;

(c) preparing a solution containing at least one cationic polymer carrying cationic groups which are capable of forming an ionic bond with the anionic or anionizable groups of the polyacrylonitrile, the cationic polymer comprising only polymer chains whose size is sufficient for them not to pass through the semipermeable membrane, and bringing this solution into contact with the surface of the semipermeable membrane intended to be placed in contact with the blood, it being possible to carry out stage (c) before or after stage (b); when the semipermeable membrane is flat, the cationic polymer solution may be sprayed onto the surface of the membrane;

(d) in the event that stage (c) is carried out subsequently to stage (b), purging the exchanger of the solution containing the cationic polymer;

(e) preparing a solution containing, in the dissolved state, at least one anticoagulant agent carrying anionic groups which are capable of forming an ionic bond with the cationic groups of the said cationic polymer, and bringing this solution into contact with the surface of the semipermeable membrane intended to be placed in contact with the blood, stage (e) being implemented after stage (c) but before or after stage (b);

(f) in the event that stage (e) is carried out subsequently to stage (b), purging the exchanger of the solution containing the anticoagulant agent.

In the event that the cationic polymer is PEI, the aforementioned stage (c) may be carried out according to the following conditions:

PEI concentration: from 0.04 to 20 g/L
medium: water; glycerinated water; saline buffers; saline solutions
pH: from 5 to 12
treatment rates (in the case of treating the membrane by circulation in the instrument): from 50 to 500 mL/min
duration: from 1 to 30 minutes
open circuit or closed circuit
under these conditions, the surface PEI concentration is between 1 and 30 mgr.

In the event that the anticoagulant agent is heparin, the aforementioned stage (e) may be carried out according to the following conditions:

heparin concentration: from 1 to 100 TU/L
medium: water; glycerinated water; saline buffers; saline solution
pH: from 5 to 10
treatment rates (in the case of treating the membrane by circulation in the instrument):from 50 to 500 mL/min
duration: from 1 to 30 minutes
open circuit or closed circuit
under these conditions, the surface heparin concentration is between 200 and 20,000 IU/m$^2$, preferably between 500 and 10,000 IU/m$^2$.

Optionally, the flat membrane or the bundle of hollow fibres is glycerinated at the end of stage (a), whence the need to de-glycerinate before undertaking the aforementioned stage (c).

Optionally, the semipermeable membrane is rinsed in order to remove the excess bound cationic polymer, either after stage (c) when stage (c) is carried out before stage (b), or after stage (d).

Optionally, the semipermeable membrane is rinsed in order to remove the excess unbound anticoagulant agent, either after stage (e) when stage (e) is carried out before stage (b), or after stage (f).

Optionally, the semipermeable membrane is re-glycerinated, depending on the case, at the end of stage (e) or (f), after the optional rinsing stages.

In the scope of the invention, the sterilization of the exchanger, without a significant effect on the composite semipermeable membrane, may be sterilization by irradiation, in particular by gamma irradiation, or sterilization with ethylene oxide. The sterilization of the exchanger may be implemented at two specific times during the method of manufacturing the exchanger.

According to a first variant, the exchanger is sterilized when the semipermeable membrane based on polyacrylonitrile carrying anionic or anionizable groups is coated with the said cationic polymer, then the treatment using the solution containing at least one anticoagulant agent is performed extemporaneously.

According to a second variant, the exchanger is sterilized when the semipermeable membrane based on polyacrylonitrile carrying anionic or anionizable groups is coated with the said cationic polymer and the said anticoagulant agent.

Other characteristics and advantages of the invention will become apparent on reading the following examples. Reference will also be made to the appended drawings and figures, in which.

The assaying methods used to evaluate the semipermeable membranes which have been described are as follows:

Treatment of the Blood Samples Prior to the Assays

The blood sampled, when leaving the dialysers, during the dialysis sessions of the following examples is immediately placed in the presence of sodium citrate which, by chelation of the calcium ions, stops any coagulation activity. The sample is then centrifuged at room temperature at 3000 revolutions per minute for 15 minutes. The supernatant plasma is collected and stored at −20° C. until the assay.

Determination of the Coagulation Time (KCT, for Kaolin-Cephalin Time)

The KCT determination is carried out using the assay kit marketed under the name C.K. PREST® by the company DIAGNOSTICA STAGO.

The KCT makes it possible to assess the lengthening of the coagulation time of a citrated plasma due to the deficit of certain coagulation factors or the presence of an anticoagulant such as heparin. In the latter case, the lengthening of the coagulation time is proportional to the amount of heparin present. The KCT determination hence makes it possible to assess the anticoagulation level of the blood. The method of measuring this coagulation time (expressed in seconds) is known, and it is carried out after recalcification and addition of an activator.

Heparin Assay in Non-Plasmatic Medium

Heparin is determined in simple media (water and electrolytes) by spectrophotometry after formation of a complex with azure A (maximum absorption at 630 nm).

Test of Extracorporeal Circulation on a Sheep:

The dialysers tested in the examples are rinsed with a physiological saline solution (heparinated or non-heparinated) circulated in the blood compartment (2 L at 200 mL/min.). The dialysate compartment is filled by ultrafiltration. Depending on the case, the sheep blood is anticoagulated by injecting heparin into the jugular vein five minutes before the start of the session. The extracorporeal blood circulation is carried out at the rate of 200 mL/min. using a HOSPAL BSM22 pump (carotid access and jugular return). The input and output pressures are recorded. The circulation is stopped when the blood pressure exceeds 500 mmHg at the entry of the dialyser, giving evidence 15 of coagulation in the circuit.

EXAMPLE 1

This example describes a method of preparing a cationic polymer, in this case a polyethyleneimine WE (PEI), aiming to remove by fractionation the smallest polymer chains (with little steric hindrance) capable of penetrating into the pores of the semipermeable membrane to be treated, and passing through it.

Figure 1:
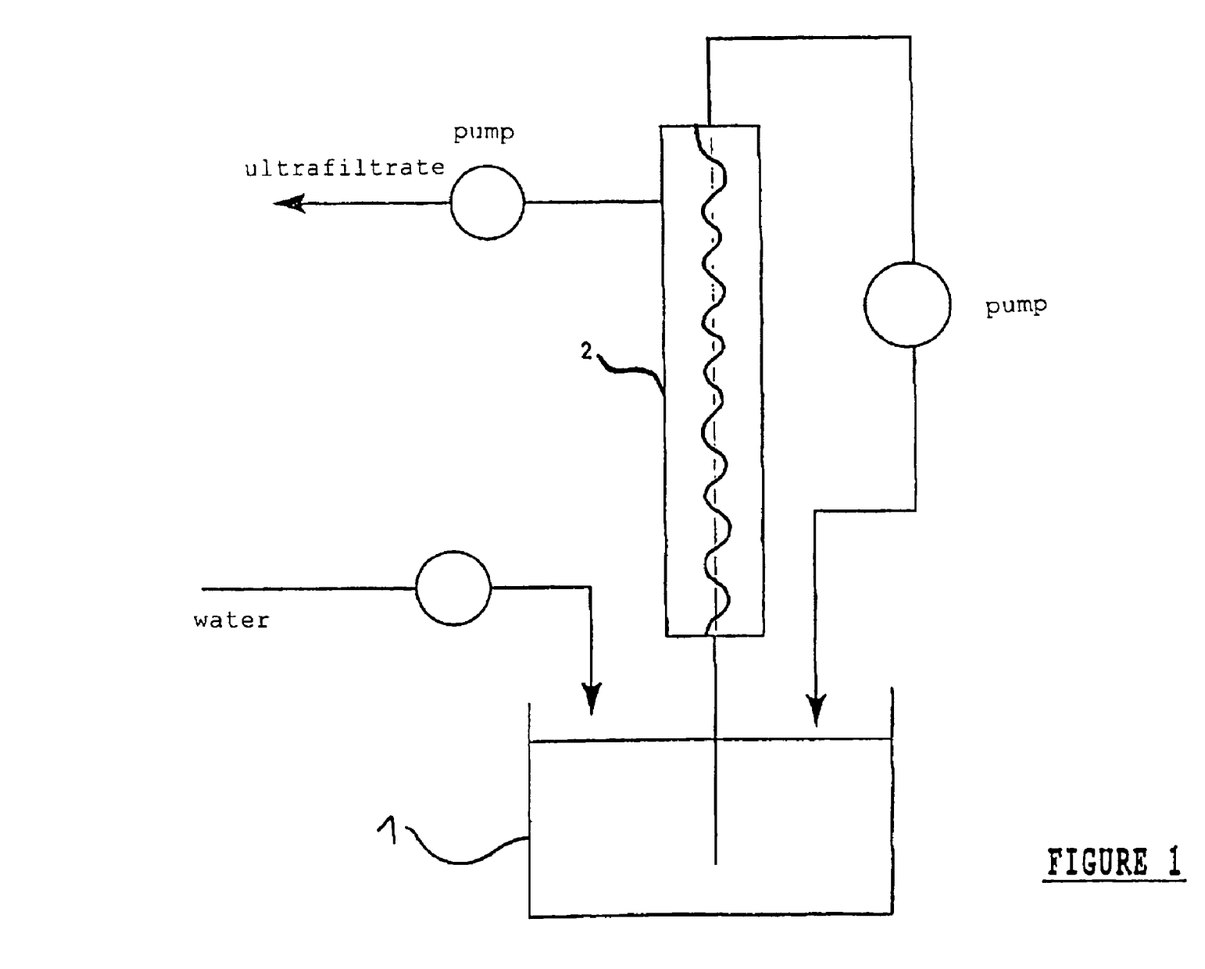
FIG. 1 represents the procedures for preparing a cationic polymer, such as polyethyleneimine (PEI), by ultrafiltration.

FIG. 1 illustrates the procedures for preparation of the PEI, which comprises the following stages:

a—preparing, in a tank 1, a solution of 1.5 liters of a solution of PEI with a weight-average molecular weight of 750 k Dalton (LUPASOL P, from BASF) and 50 g per liter, in distilled water;

b—circulating, in a closed circuit, the solution in the blood compartment of a dialyser 2 with hollow fibres (brand name FILTRAL 16, manufactured by the company HOSPAL INDUSTRIE, France), equipped with a membrane (working area of 1.6 m$^2$) made of AN69 35 (copolymer of acrylonitrile and sodium methallyl sulphonate), at the raze of 300 ml per minute;

c—simultaneously with stage b, ultrafiltration at the rate of 60 ml per minute with addition of water into the tank 1, at the same rate.

The duration of the preparation is 156 minutes.

The assay of the PEI present in the ultrafiltrate is determined in water by spectrophotometry after formation of a coloured complex with cobalt II thiocyanate (maximum absorption at 304 nm).

Figure 2:
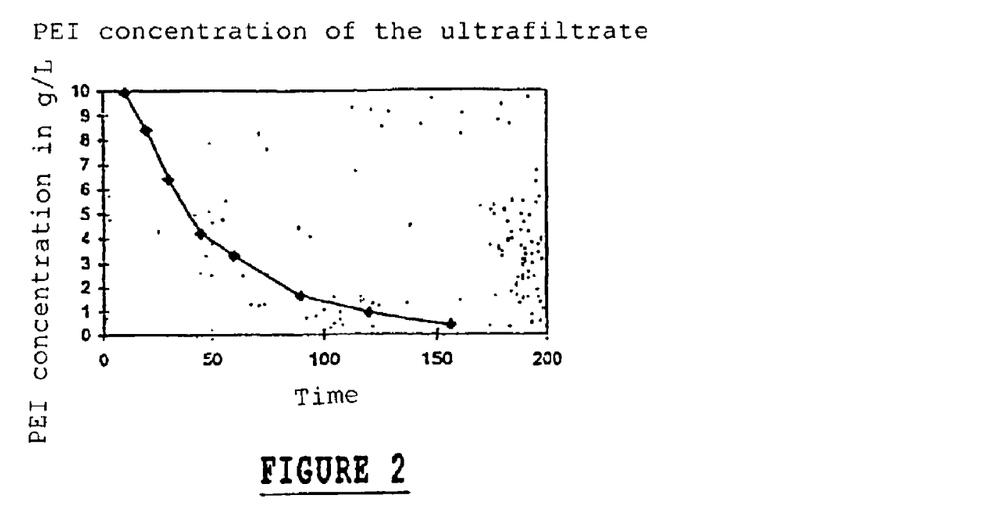
FIG. 2 represents the change in the PEI concentration in the ultrafiltrate.

The change in the PEI concentration in the ultrafiltrate is given on appended FIG. 2.

Under the conditions of the aforementioned method, the amount of PEI removed by ultrafiltration is 32 g, which represents 43% of the original PEI.

Figure 3:
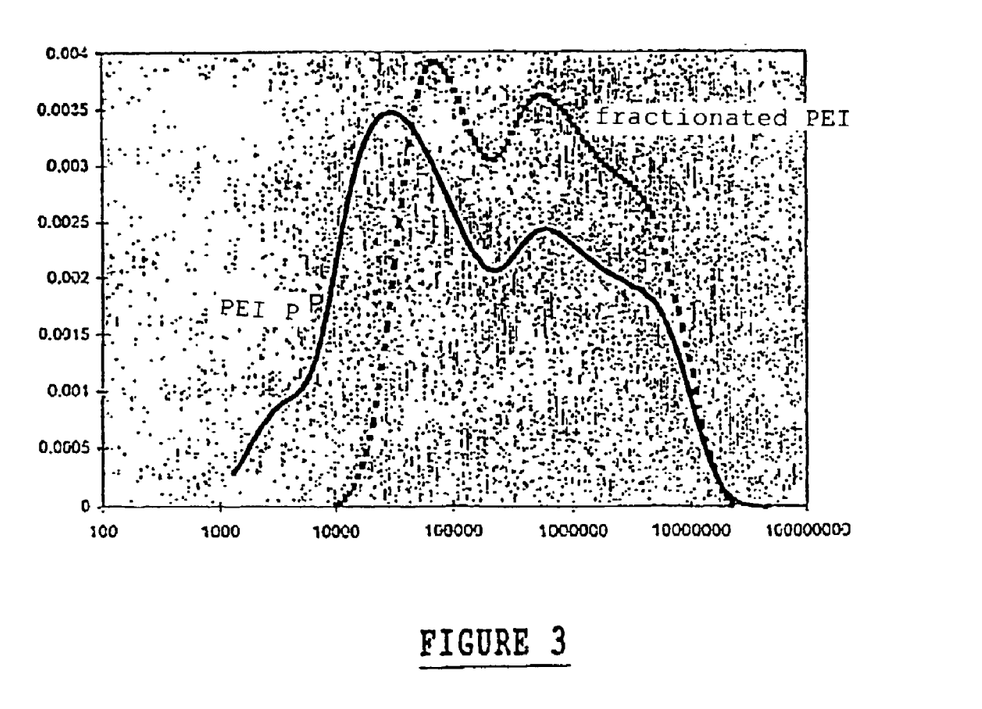
FIG. 3 represents the distribution of the weight-average molecular weights of the non-fractionated PEI, denoted PEI P, (LUPASOL P, from BASF) and fractionated PEI.

The distribution by molecular weight (Mw) of the non-fractionated PEI (denoted PEI P) and the fractionated PEI is determined by a steric exclusion chromatograph (ultrahydrogel column from the company WATERS) and is represented on appended FIG. 3. FIG. 3 shows that the molar mass of the smallest chains of fractionated PEI is of the order of 10,000 g/mole.

EXAMPLES 2

Reference Example 2a

A dialyser with a flat membrane made of AN69 (brand name CRYSTAL 4000, manufactured by HOSPAL INDUSTRIE, France), having a working area of 1.5 m$^2$ and sterilized by gamma irradiation, is rinsed by circulating, in the blood compartment, 2 liters of physiological saline containing 5000 IU of non-fractionated heparin.

An extracorporeal blood circuit comprising the dialyser is then connected to the vascular circuit of a sheep. No anticoagulant is injected into the sheep's blood.

Figure 4:
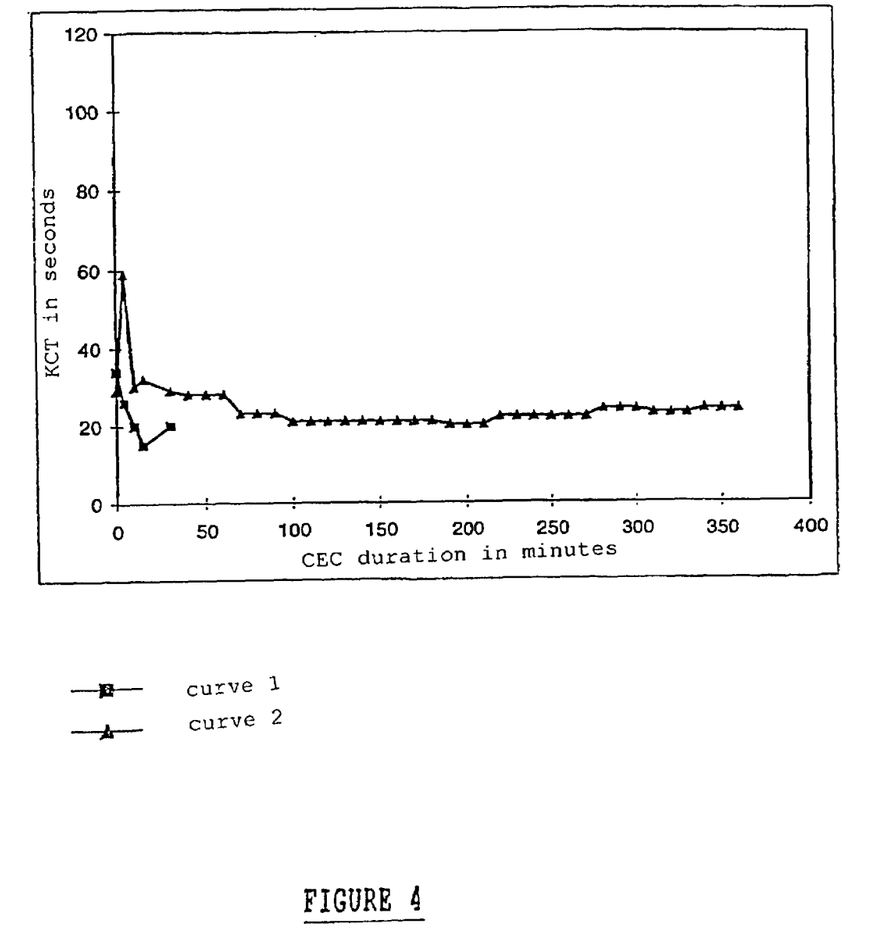
FIG. 4 represents the change in the coagulation time (KCT) of sheep blood subjected to an extracorporeal circulation test using a dialyser with a flat AN69 membrane treated with fractionated PEI, gamma-sterilized, then treated extemporaneously with heparin.

On FIG. 4, curve 1 gives the chance in the KCT during the 30 minutes of the blood circulation. Coagulation took place at the end of 30 minutes.

Example 2b According to the Invention

A dialyser was manufactured according to the invention by the company HOSPAL INDUSTRIE (France). One face of a flat membrane made of AN69, having a working area of 1.5 m$^2$, is treated by spraying fractionated PEI (see Example 1) at the concentration of 5 g/kg into a 40/60 by weight water/glycerol mixture. The amount of fractionated PEI deposited is 10 mg/m$^2$.

This membrane is fitted in a dialyser so that the treated face is oriented towards the blood compartment of the dialyser.

The dialyser is then sterilized by gamma irradiation (36 K Gy).

Just before its use, the sterilized dialyser is rinsed using a solution of physiological saline and non-fractionated heparin, as indicated in Reference Example 2a.

An extracorporeal blood circuit comprising the dialyser is then connected to the vascular circuit of a sheep. No anticoagulant is injected into the sheep's blood.

It was possible to circulate the sheep's blood for 6 hours in the extracorporeal circuit without coagulation taking place (the termination after 6 hours is voluntary and does not correspond to coagulation in the circuit). Curve 2 of FIG. 4 gives the KCT level throughout the circulation. The KCT remains at a normal level, signifying that heparin is not released, whereas a KCT of more than 100 seconds is customarily necessary for correct operation of a blood treatment in an extracorporeal circulation circuit.

EXAMPLES 3

Reference Example 3a

A dialyser (brand name FILTRAL 20, manufactured by HOSPAL INDUSTRIE, France), equipped with a bundle of hollow AN69 fibres with a working area of 2 m$^2$, sterilized with ethylene oxide, is rinsed by circulating, in the blood compartment, 2 liters of physiological saline containing 10,000 IU of non-fractionated heparin.

An extracorporeal blood circuit comprising the dialyser is then connected to the vascular circuit of a sheep, after 5000 IU of non-fractionated heparin have previously been injected into the sheep.

The coagulation of blood in the extracorporeal circuit took place after the blood had circulated therein for 2 hours.

Figure 5:
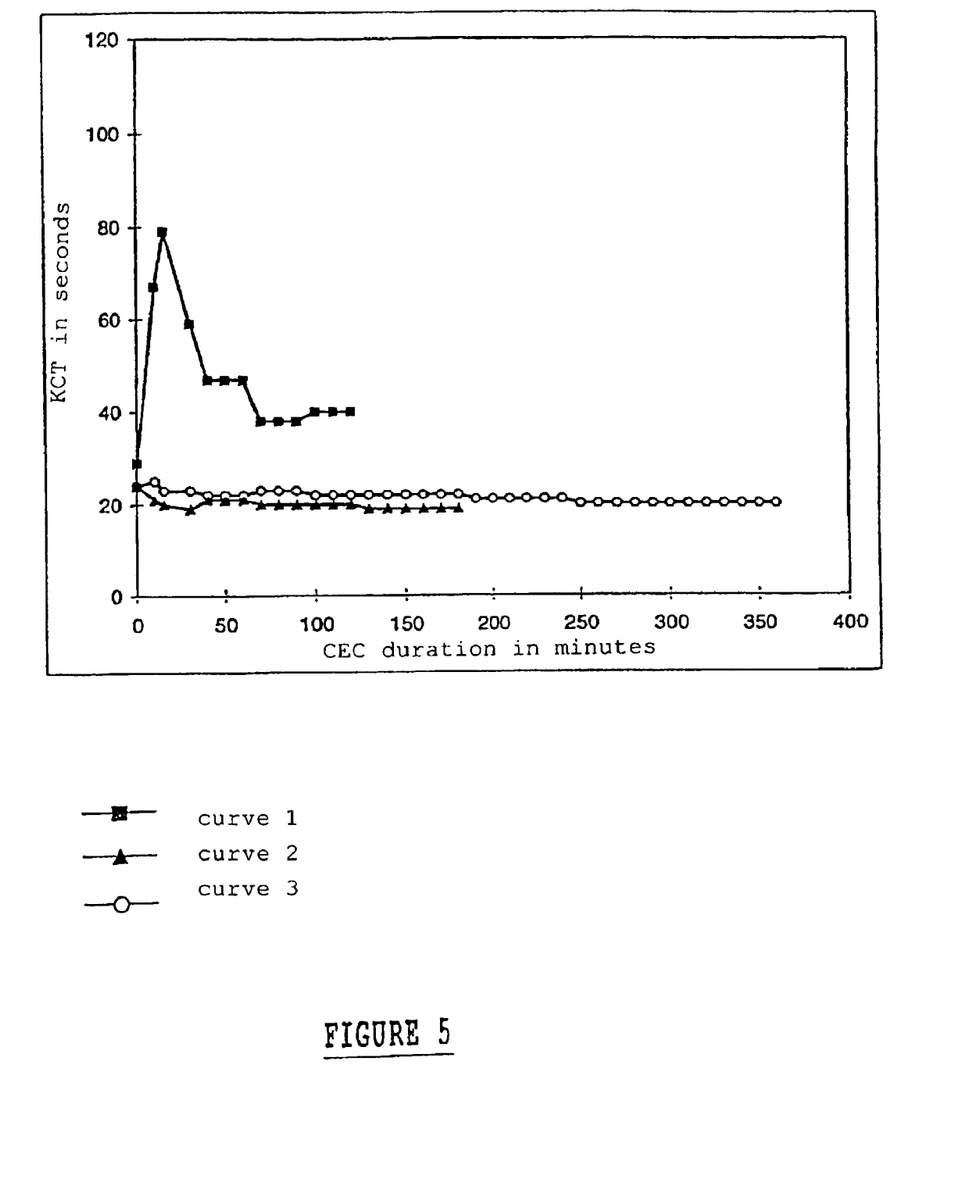
FIG. 5 represents the change in the coagulation time (KCT) of sheep blood subjected to an extracorporeal circulation test using a dialyser with hollow AN69 fibres treated with fractionated PEI, then heparinated, and finally gamma-sterilized before use.

The change in the KCT level is represented on FIG. 5, by curve 1.

Example 3b According to the Invention

A dialyser (brand name NEPHRAL 300, manufactured by HOSPAL INDUSTRIE, France), equipped with a bundle of hollow AN69 fibres with a working area of 1.3 m$^2$, is treated by circulating, in the blood compartment, a solution of fractionated PEI prepared as in Example 1 (1 g/L in water, closed circuit on 200 mL, 5 minutes, 200 mL/min.). This dialyser undergoes a second treatment by circulating, in the same compartment, a solution of non-fractionated heparin (5 IU/mL in a phosphate solution ($Na_2HPO_4$ at 10 mM) closed circuit on 3 L, 200 mL/min., 5 or 30 min.). The dialyser is then purged with air (0.3 bar for 30 s) Under these conditions, the amount of PEI bound is of 2 the order of 15 mg/m$^2$, the amount of heparin bound is 2500 and 6800 IU/m$^2$ (measured according to the method of assaying heparin in a non-plasmatic medium).

This dialyser is then sterilized by gamma as irradiation. Just before the dialyser is used, 2 liters of physiological saline are circulated in the blood compartment in order to rinse it. An extracorporeal blood circuit comprising the dialyser is then connected to the vascular circuit of a sheep. No anticoagulant is injected into the sheep's blood.

It was possible to maintain the circulation of blood in the extracorporeal circuit without injecting heparin into the extracorporeal circuit for 3 and 6 hours without coagulation making place, and curves 2 and 3 of FIG. 5 indicate that the KCT levels remained normal.

EXAMPLES 4

Examples 4 correspond to series of clinical trials carried out with dialysers according to the present invention and dialysers not according to the present invention.

Comparative Examples 4a and 4b

4a) Untreated dialysers of brand name NEPHRAL 300 are used in a series of clinical trials carried out under the following conditions:
- 6 patients;
- 108 haemodialysis sessions lasting 4 hours with addition of heparin;
- prior to each haemodialysis session, the dialyser is rinsed by circulating 1 liter of a physiological saline solution containing 5000 IU of heparin in the blood compartment of the dialyser;
- at the end of each haemodialysis session, the blood is returned to the patient by rinsing the blood compartment of the dialyser with 1 liter of physiological saline.

4b) Dialysers of brand name NEPHRAL 300 were treated successively in the following way:
- circulating 1 liter of water, with a flow rate of 200 ml/min, in the blood compartment of the dialyser in order to remove the glycerine present in the hollow fibres;
- circulating 1 liter of a solution of non-fractionated PEI with a weight-average molecular weight of 750 K Dalton (LUPASOL P from BASF), in the blood compartment of the dialyser;
- purging with air;
- sterilizing by gamma irradiation;
- prior to each haemodialysis session, the dialyser is rinsed by circulating 1 liter of a physiological saline solution containing 5000 IU of heparin in the blood compartment of the dialyser;
- at the end of each haemodialysis session, the blood is returned to the patient by rinsing the blood compartment of the dialyser with 1 liter of physiological saline.

A series of 27 clinical trial sessions is carried out with these dialysers.

Results of the Series of Clinical Trials (4a) and (4b)

After returning the blood, the dialysers are evaluated visually, on a scale of 1 to 4:
- score 1 (poor): the colour of the entire dialyser is red and indicates significant coagulation of the blood in the semipermeable membrane;
- score 2 (medium): the colour of approximately half the dialyser is red;
- score 3 (good): only a few red traces in the dialyser;
- score 4 (excellent): the dialyser is not red.

|  | Example 4a | Example 4b (*) |
|---|---|---|
| Average value over all the sessions of the amount of heparin added, without including the amount of heparin bound at the time of rinsing (min value, max value) (**) | 6200 (min: 3000) (max: 8000) | 8400 (min: 4500) (max: 12000) |
| Average value over all the sessions of the visual assessment of the dialysers (min value, max value) | 3.0 (min: 2) (max: 4) | 1.9 (min: 1) (max: 3) |

(*) the amount of non-fractionated PEI bound is of the order of 100 mg/m$^2$ and the amount of heparin bound, at the time when the dialyser is rinsed, is of the order of 2000 IU/m$^2$ of membrane.
(**) the amount of heparin added makes it possible to maintain the KCT between 90 and 120 s.

Conclusion

The treatment with a non-fractionated PEI leads to significant consumption (adsorption) of heparin. Furthermore, the absorbed heparin is not active since the dialysers thus treated in Examples (4b) lead to coagulation problems.

Examples 4c According to the Present Invention

A flat membrane made of AN69 is treated by spraying fractionated PEI, prepared under the conditions described above in Example 1, in a proportion of 10 mg/m$^2$ of membrane.

Dialysers of the CRYSTAL type are fitted with this membrane (1.25 m$^2$ working surface of membrane per dialyser) and are sterilized by gamma irradiation.

A series of clinical trials is carried out with these dialysers under the following conditions:
- 13 patients;
- 256 haemodialysis sessions;
- prior to each haemodlalysis session, the dialyser is rinsed by circulating 2 liters of a physiological saline solution containing 5000 IU of heparin per liter in the blood compartment of the dialyser;
- haemodialysis sessions lasting 4 hours with or without addition of heparin (see table);
- at the end of each haemodialysis session, the blood is returned to the patient by rinsing the blood compartment of the dialyser with 1 liter of physiological saline.

| Average value over all Examples (4c) of the amount of heparin added, without including the amount of heparin bound at the time of rinsing (*) | 6000 | 5000 | 4000 | 3000 | 2000 | 1000 | 0 |
|---|---|---|---|---|---|---|---|
| Average value over all the sessions of the visual assessment of the dialysers (number of sessions) | 4 (39) | 4 (39) | 4 (38) 2 (1) | 4 (35) 2 (2) 1 (1) | 4 (31) 2 (4) | 4 (28) 2 (4) 1 (1) | 4 (28) 2 (4) 1 (1) |

(*) the amount of heparin bound at the time of rinsing is of the order of 1500 IU/m$^2$ of membrane.

Conclusion

The treatment with a fractionated PEI, followed by a treatment with heparin, makes it possible to carry out dialysis with lower amounts of anticoagulant injected into the patient.

Comments

In comparative Examples (4a) and (4b), the KCT is kept between 90 and 120 s.

In Examples (4c), it is the injected heparin dose which is fixed (between 0 and 6000) and, in all cases, the KCT at the end of a session is less than 50, which is a considerable advantage for the patient (no more heparin circulating at the end of dialysis, and therefore no more risk of haemorrhaging).

After return of the blood, the dialysers of this series of clinical trials are evaluated as previously under the conditions described above for Examples (4a) and (4b).

The invention claimed is:

1. A method for reducing the thrombogenic character of an exchanger for treating blood or plasma by extracorporeal circulation, comprising two compartments separated by a semipermeable membrane having a surface oriented towards a first compartment intended for the circulation of blood or plasma, the method comprising:
    (a) preparing a semipermeable membrane, in the form of a flat membrane or a bundle of hollow fibres, from a solution of polyacrylonitrile carrying anionic or anionizable groups;
    (b) assembling the various components of the exchanger, in particular fitting the semipermeable membrane or a bundle of hollow fibres in a case;
    (c) preparing a solution containing at least one cationic polymer carrying cationic groups that form ionic bonds with the anionic or anionizable groups of the polyacrylonitrile, the cationic polymer further comprising only polymer chains whose size is sufficient for the chains not to pass through the semipermeable membrane, and bringing this solution into contact with the surface of the semipermeable membrane intended to be placed in contact with the blood or plasma, stage (c) being carried out before or after stage (b);
    (d) in the event that stage (c) is carried out after stage (b), purging the exchanger of the solution containing the cationic polymer;
    (e) preparing a solution containing, in the dissolved state, at least one anticoagulant agent carrying anionic groups that form ionic bonds with the cationic groups of said cationic polymer, and bringing this solution into contact with the surface of the semipermeable membrane intended to be placed in contact with the blood, stage (e) being implemented after stage (c) but before or after stage (b);
    (f) in the event that stage (e) is carried out after stage (b), purging the exchanger of the solution containing the anticoagulant agent; and
    (g) sterilizing the exchanger once the semipermeable membrane based on polyacrylonitrile carrying anionic or anionizable groups is coated with the cationic polymer and the anticoagulant agent.

2. A method according to claim 1, wherein said cationic polymer is polyethyleneimine, the amount of which brought into contact with the semipermeable membrane being between approximately 1 mg and approximately 30 mg per m$^2$ of membrane (including end points).

3. A method according to claim 1, wherein the cationic polymer is prepared by ultrafiltration using a separate semipermeable membrane which is identical to the semipermeable membrane or which has a cut-off threshold equal to or greater than that of the semipermeable membrane, in order to preclude said chains of the cationic polymer from passing through the semipermeable membrane.

4. A method according to claim 1, wherein said anticoagulant agent consists essentially of heparin, the amount of which brought into contact with the semipermeable membrane being between approximately 200 IU and approximately 20,000 IU per m$^2$ of membrane (including end points).

5. A method according to one of claims 1–4, wherein said step of sterilizing the exchanger further includes sterilizing the semipermeable membrane with gamma irradiation or with ethylene oxide.

* * * * *

UNITED STATES PATENT AND TRADEMARK OFFICE
CERTIFICATE OF CORRECTION

PATENT NO. : 7,056,458 B2 Page 1 of 1
APPLICATION NO. : 09/937558
DATED : June 6, 2006
INVENTOR(S) : Crost et al.

It is certified that error appears in the above-identified patent and that said Letters Patent is hereby corrected as shown below:

On the title page, item (57), line 10, "concern" should read --concerns--.

On the title page, item (57), line 13, "semipermeable, membrane" should read --semipermeable membrane--.

Signed and Sealed this

Fifth Day of September, 2006

JON W. DUDAS
*Director of the United States Patent and Trademark Office*